United States Patent [19]

deWalle et al.

[11] Patent Number: 4,547,962

[45] Date of Patent: Oct. 22, 1985

[54] METHOD OF MAKING EDDY-CURRENT PROBES

[75] Inventors: Stewart deWalle; Richard T. deWalle, both of Rexdale, Canada

[73] Assignee: Miep Holdings Inc., Rexdale, Canada

[21] Appl. No.: 433,294

[22] Filed: Oct. 7, 1982

[30] Foreign Application Priority Data

Oct. 9, 1981 [CA] Canada .................................. 387668

[51] Int. Cl.$^4$ .......................................... H01F 41/00
[52] U.S. Cl. ................. 29/606; 264/272.19; 324/240; 324/262
[58] Field of Search ............ 29/602 R, 606; 324/237, 324/238, 240, 243, 262; 264/272.19

[56] References Cited

U.S. PATENT DOCUMENTS 3,004,215 10/1961 Datt et al. ...................... 324/238 X
3,304,599 2/1967 Nordin ............................ 29/606 X
3,378,917 4/1968 Lapham ....................... 264/272.19 X Primary Examiner—Carl E. Hall Attorney, Agent, or Firm—Hirons, Rogers & Scott

[57] ABSTRACT

In a new method of manufacturing eddy-current probes, particularly such probes for the scanning of a test surface generated by a non-flat profile, a thin, flexible support layer is laid against the test surface so that it conforms exactly thereto. One or more test coils have a sector thereof laid against the back face of the support layer so that the coil sector also conforms to the same profile in the plane of the coil and the profile. A plurality of separate ferrite core elements are now laid inside the loop of the coil, or the loops of the coils, and pressed against the coil so as to form a core that also conforms to the profile to be scanned. The remainder of the coil (or coils) is pressed against the backs of the ferrite elements and the assembly is encapsulated to make it rigid enough for mounting in a test apparatus for scanning over the surface to be tested. The front face of the support layer is the "active" surface of the probe and conforms precisely with the profile, since it was generated thereby.

7 Claims, 9 Drawing Figures

METHOD OF MAKING EDDY-CURRENT PROBES

FIELD OF THE INVENTION

The present invention is concerned with a new method of making eddy-current probes.

REVIEW OF THE PRIOR ART

Non-destructive testing of metal parts for the presence of flaws, pits, cracks, etc., by use of an eddy-current probe is now of course a well-established industry. Such probes consist for example of a solid cylindrical core of a ferrite material carrying a coil of wire; the impedance of the coil is monitored as the tip of the core is moved over the metal piece under test and flaws, etc. are detected by the change in coil impedance as the tip moves over the flaw. A typical size for such a core is about 1.5 mm diameter and the area over which it can detect a flaw is about 2 mm diameter, so that a large specimen must be scanned repeatedly if it is to be examined over its entire surface; such repeated scanning is of course a lengthy and tedious procedure, even when effected automatically by a machine.

One way in which the number of scans has been reduced is to use an assembly of a number of probes or coils which are moved together over the surface. However there is a practical limit to how close the probes can be packed and the operator accepts the risk that a flaw will be missed because it is small enough to be "scanned" by the space between the probes without affecting any of them. Another way is to make the probe larger, which involves the production of a larger core; this solution is in commercial practice only really suitable for specimens with flat surfaces. Thus, if the surface is not flat the core must be shaped accordingly, which limits its application to exactly similar specimens. Moreover ferrite is an expensive material that is difficult to machine, so that the probes become correspondingly costly.

DEFINITION OF THE INVENTION

It is therefore an object of the invention to provide a new method of making eddy-current probes.

It is a specific object to provide such a method that is particularly suitable for making probes for the scanning of nonflat profiled surfaces.

In accordance with the present invention there is provided a method of making an eddy-current probe for the scanning of a test surface having a corresponding profile in a plane which intercepts the test surface so as to include the profile, the method including the steps of:

(a) applying to the test surface so as to be intercepted by the plane, and so as to conform to the test surface profile, a support member having parallel front and back surfaces with the front surface immediately adjacent to the test surface, (b) applying to the support member back surface so as to be intercepted by the plane, and so as to conform to said test surface profile, a first portion of a probe electrical test coil, and (c) mounting inside the electrical test coil immediately adjacent to the said first portion of said test coil a plurality of separate ferrite core elements so as to be intercepted by the plane and so as to conform to said test surface profile.

DESCRIPTION OF THE DRAWINGS

Eddy-current probes that are particular preferred embodiments of the invention will now be described, by way of example, with reference to the accompanying diagrammatic drawings, wherein.

DESCRIPTION OF THE PREFERRED EMBODIMENTS

The application of the process of the invention to the non-destructive testing of an airplane wheel has been selected to illustrate the invention, but is not intended in any way to limit the invention, which is of general application to the manufacture of eddy-current probes. Thus, the invention is particularly suitable for the production of probes intended for the scanning of surfaces that have been generated by a non-flat profile, but it is also suitable for the manufacture of probes intended for the scanning of flat profiles.

Aircraft wheels are subjected to regular non-destructive testing because of the high stresses to which they are subjected on take-off, landing and particularly taxiing. Under these conditions small flaws such as corrosion pits can lead quickly to the formation of hair-line cracks, which can then develop into major faults resulting for example in parts of the rim breaking away from the wheel. A wheel is a particular example of a shape that is generated by a profile, which in this case is rotated about a centre. Other articles can of course be generated as the result of a profile moving in some other mode, such as along a straight line.

Figure 2:
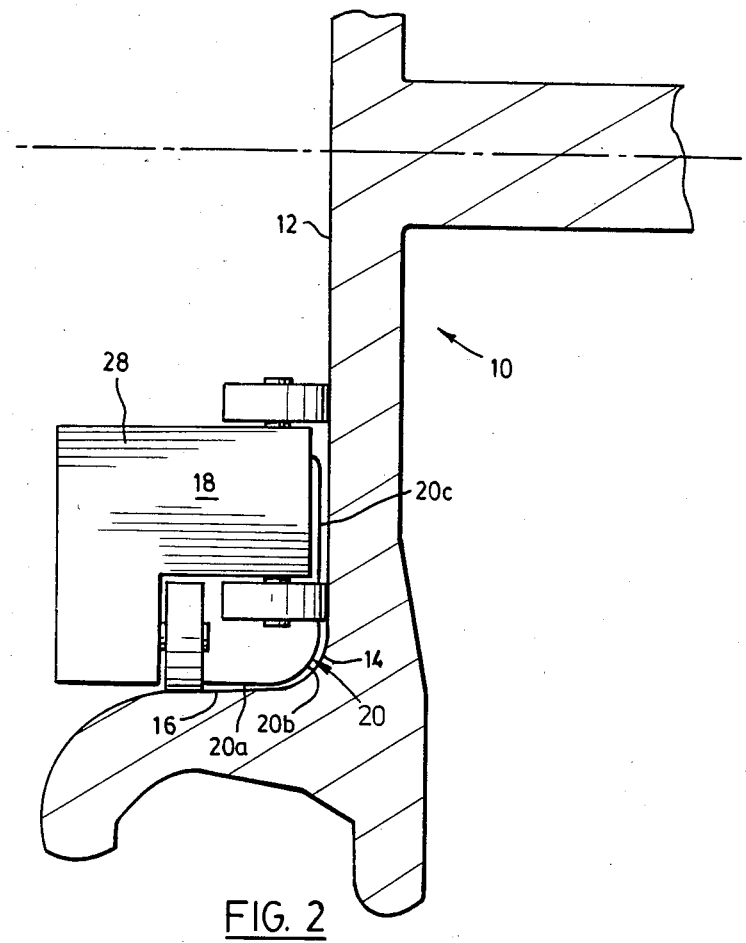
FIG. 2 is a enlarged cross-sectional view through the rim of a vehicle wheel to be tested on the apparatus of FIG. 1, and illustrating the use therein of a probe manufactured by the method of the invention.

The profile in question is somewhat complex, as will be seen by reference to a section of a wheel section 10 shown in FIG. 2, consisting of a relatively long flat bead seat 12 that is connected by a concave bead seat radius 14 to a bead seat rim 16. The wheels of different aircraft types usually have different profiles. Fortunately it is only necessary in practice to examine the bead seat radius and the immediately adjoining portions of the bead seat 12 and bead seat rim 16, but this does require the use of a probe that can scan from the relatively flat bead seat 12 through the seat radius 14 and thence again to the lower part of the convex bead seat rim 16. Such scanning can be performed by a probe 18 manufactured in accordance with the invention and having an active surface 20 that conforms to the bead seat radius and to the immediately adjoining parts 20a, 20b and 20c of the bead seat and bead seat rim.

Figure 1:
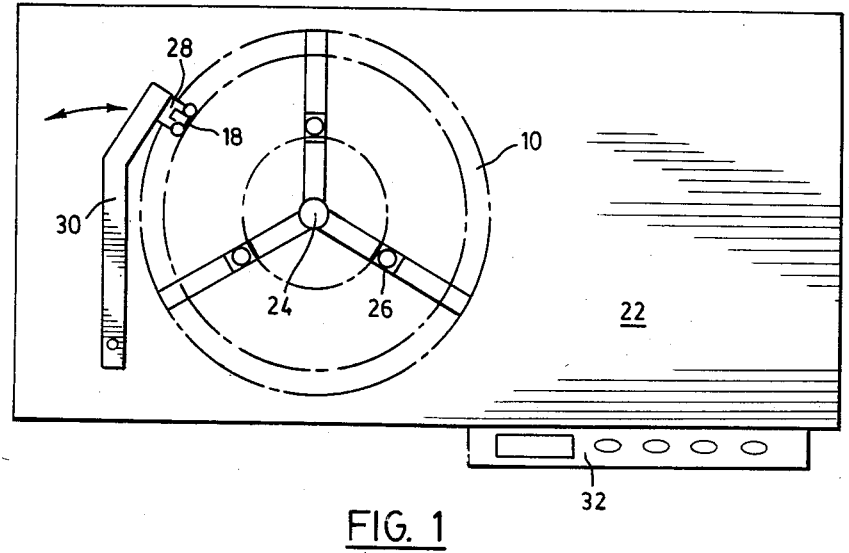
FIG. 1 is a plan view of an apparatus employing an eddy-current probe of the invention in the testing of a vehicle wheel for defects, such as an airplane wheel.

The test apparatus illustrated by FIG. 1 consists of a table 22 on which the wheel 10 can be mounted so as to be rotated about a vertical axis 24 by means of a clamp support structure 26 of any convenient form. The probe 18 is mounted in a wheeled carriage 28 which is in turn mounted on one end of a universally-movable articulated arm 30 that is spring-biased in any convenient manner to urge the wheeled carriage into engagement with the wheel periphery, so that the carriage will run freely on the wheel periphery, with the probe active surface in close proximity to the wheel surface, as the wheel is rotated about the axis. After each complete rotation of the wheel, or progressively as the wheel rotates, the probe is moved vertically by corresponding movement of the arm, so that the entire surface to be examined is scanned by the probe. The results of the scan are displayed and recorded by instruments on panel 32.

The exact construction of the test apparatus and the electrical equipment connected to the probe are not important to the description of this invention and are not further described.

Thus, the invention provides a relatively simple and inexpensive method of manufacturing a test probe having an active surface which in this case is convex and conforms sufficiently accurately to the surfaces to be tested. Thus, the surface 20 has a central convex portion 20b that conforms to the bead seat radius and an end slightly convex portion 20a that conforms to the adjacent part of the bead seat rim sufficiently for the probe to be moved the necessary small amount up that part. The other end portion 20c is flat and the probe can therefore be moved along the relatively flat bead seat in order to scan it.

As can be best seen in FIGS. 5a-5d, the probe is made in accordance with the invention by first applying a thin flexible support strip 34 to the profile to be tested, so that the length of the strip is parallel to the plane of the profile and so that the strip 34 assumes the profile required for the probe active surface. The strip 34 is simply laid in position on the test surface with its front face contacting the surface, and, if necessary, is tacked in position with a suitable adhesive to facilitate the subsequent steps of the process.

A flexible test coil 36 is formed, usually by pile winding a plurality of turns of the wire such that the required impedance is obtained and then a portion of the coil of complementary shape to the strip is laid against the back surface of the support strip in the said plane so that the portion also conforms to the profile of the test surface and the support strip 34. Conveniently during its winding adhesive is applied to the coil 36 to adhere the windings thereof together; if a slight excess is used this can be used to adhere the coil sector to the support member back surface.

In this particular embodiment a second test coil 38 of similar shape to the coil 36 is disposed parallel to the coil 36 but spaced therefrom to provide a balanced electrical circuit. This second coil 38 also has a sector complementary portion thereof laid against the back face of the support members so as to conform to the profile in a plane parallel to the plane of the coil 36.

A plurality of separate ferrite core elements 40 are now inserted within the loops of the coils 36 and 38 so as to extend through both coils transversely to the planes of the two coils, the cores being pressed against the portions adjacent the support member back surface so that together they form an effective electromagnetic ferrite core of shape conforming to the profile. The remaining portions of the coils are now pressed into close contact with the respective back portions of the core faces to give a laminated structure for maximum electromagnetic effect.

Figure 3:
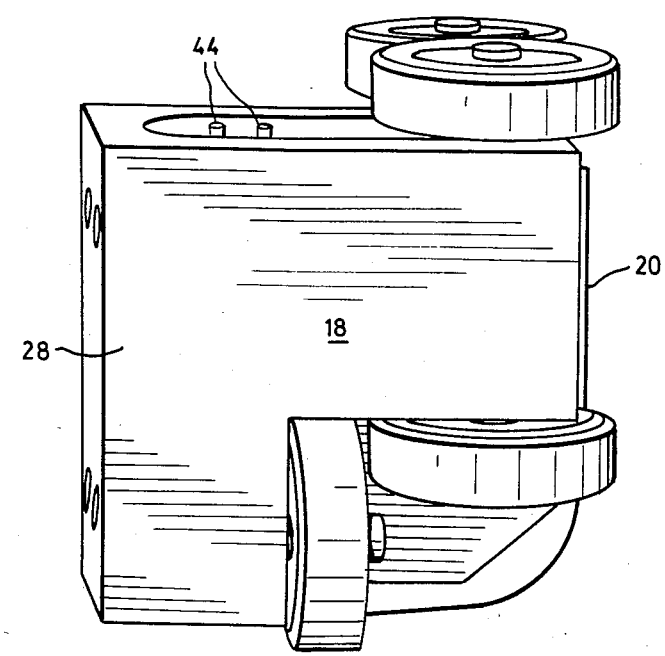
FIG. 3 is a perspective enlarged view showing a probe of the mounted in a carriage for use in the apparatus of FIG. 1.
Figure 4:
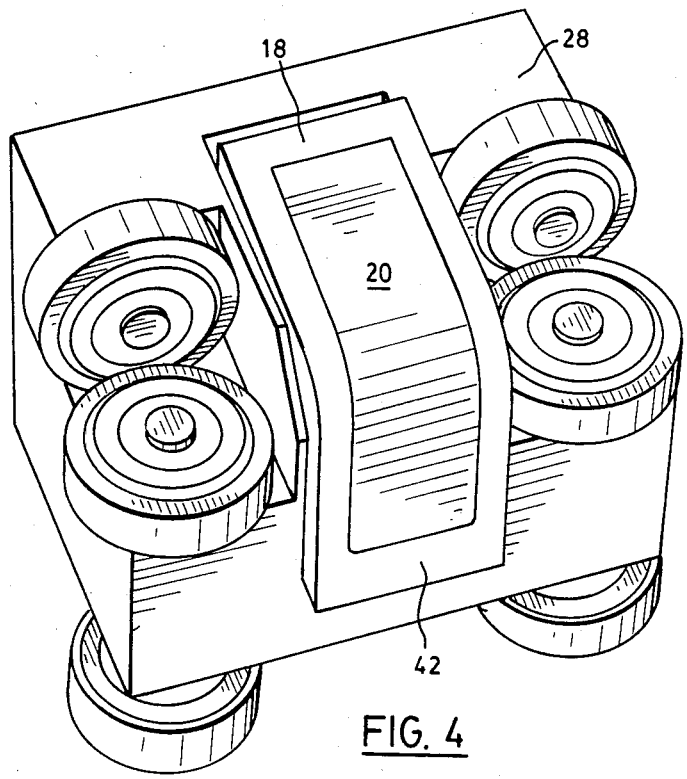
FIG. 4 is a perspective view showing the opposite side of the probe and carriage of FIG. 3, FIGS. 5a to 5d are cut-away progressive perspective views to illustrate the method of the invention.
Figure 5:
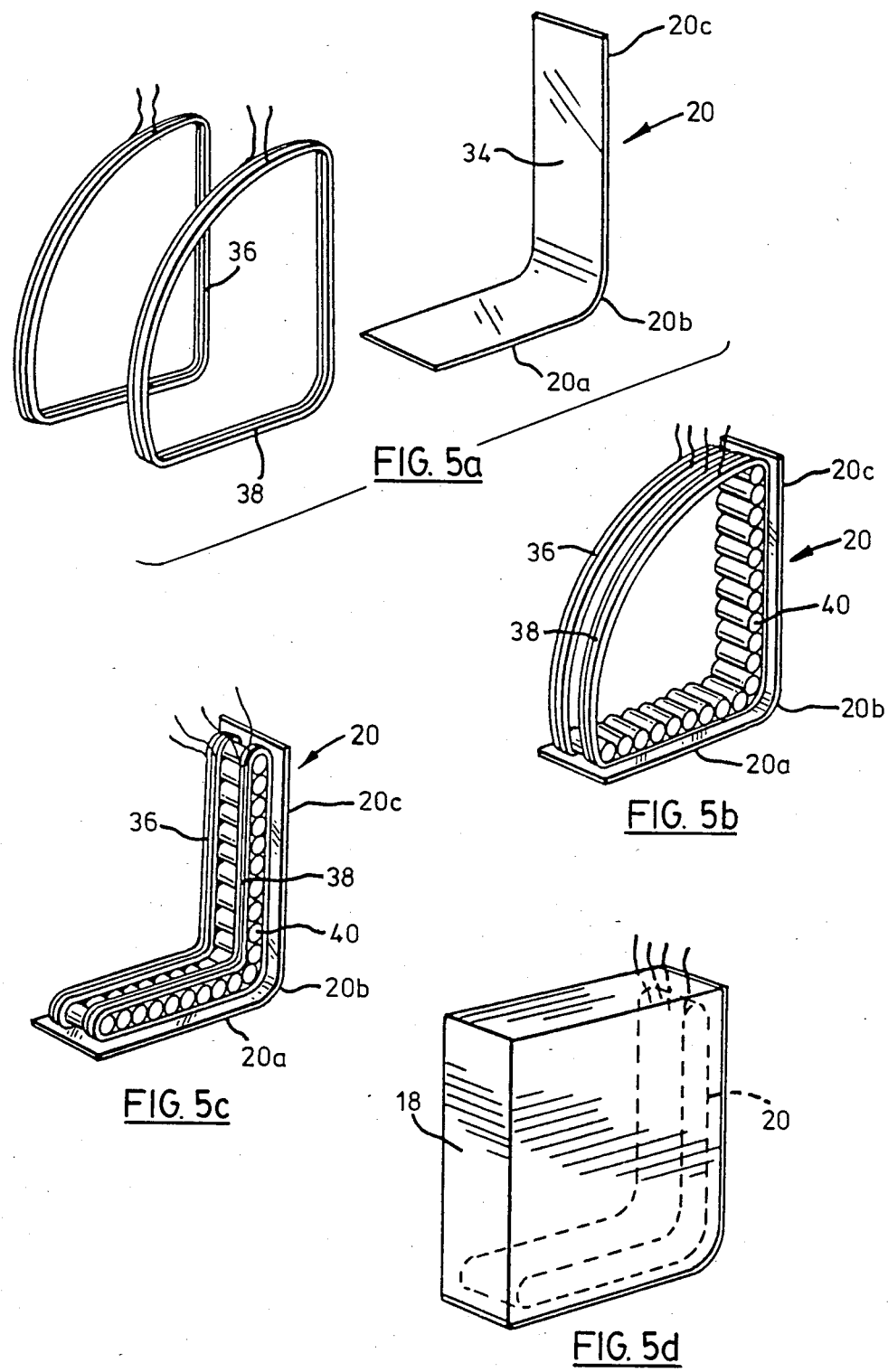

As can best be seen in FIGS. 3 and 4 the assembly is now surrounded by a rigid metal support frame 42 having terminals 44 for the coil ends and the interior open space filled with an encapsulating resin to hold the assembly firmly in place in the frame. When the resin has set the probe is removed from the surface and is ready for use, subject only to optional clean-up items such as removal of resin flash and polishing of the front active surface to ensure that it will move easily over the surface to be tested.

Since the active surface was formed in contact with the surface to be tested then it has an accurately formed complementary profile. Its mounting in the carriage will usually be such that it is spaced about 0.2 mm from the surface to be tested. Although in this embodiment a non-flat concave profile probe is described it will be apparent that the invention is also applicable to the manufacture of probes for use on convex or flat surfaces, in the latter case the invention providing an extended test surface reducing the number of scans to be employed, without the need for a costly and fragile specially formed unitary ferrite core.

In this particular embodiment the total length of the probe active surface was about 5 cm and the support layer was formed from a piece of polyester plastic tape of about 0.075 mm (0.003 in.) thickness. Each coil was wound to have an impedance of about 50 ohms at 70 kiloherz, the resulting coils having a cross-section perpendicular to the said plane that is 0.127 mm (0.005 in.) thick. The ferrite coils were of circular cross-section of 1.5 mm diameter (0.060 in.) and 6.35 mm (0.25 in.) length, the two coils being spaced about 1.60 mm (0.0625 in.) apart; twenty such cores were used placed with their circumferences touching their immediately adjacent cores.

Although the cores employed in this embodiment are of circular cross-section, cores of other cross-sections can of course be used although the circular form has the advantage that the core peripheries can be made to touch one another for magnetic continuity and provide a relatively continuous-appearing surface irrespective of the complexity of the profile, and whether or not it includes convex and/or concave portions.

Figure 6:
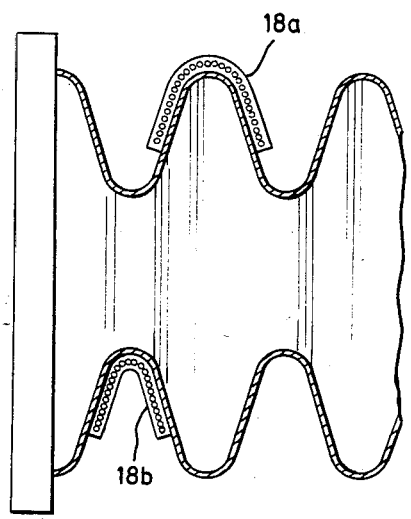
FIG. 6 is a cross-section through a bellows structure to be tested to show other applications of embodiments of the invention.

FIG. 6 illustrates the complete flexibility of the invention in the manufacture of probes for differing shapes. Thus, one product requiring testing is metal bellows that in operation are subjected to pressure, mechanical flexing, temperature variations and the like, which can result in the development of cracks and consequent leakage. By the application of the invention it is possible to provide relatively easily and inexpensively and extremely concave-curved probe 18a and an extremely convex-curved probe 18b which together permit rapid inspection of the surface of the bellows. Each probe can have one or more coils, as is required for the test equipment to be employed and in each the ferrite cores can be of any suitable cross-section. The choice of core cross-section follows from the desire to provide the maximum amount of core inside the coils, and to this end various shapes can be employed and different shapes may be used at different parts of the same probe.

The embodiments of the invention in which an exclusive property or privilege is claimed are defined as follows:

1. A method of making an eddy-current probe for the scanning of a test surface having a corresponding nonflat profile in a plane which intercepts the test surface so as to include the profile, the method including the steps of:
- (a) applying to said test surface so as to be intercepted by the plane, and so as to conform to the test surface profile, a support member having parallel front and back surfaces with the front surface immediately adjacent to the test surface,
- (b) applying to the support member back surface so as to be intercepted by the plane, and so as to conform to said test surface profile, a first portion of a probe electrical test coil, and
- (c) mounting inside the electrical test coil immediately adjacent to the said first portion of said test coil a plurality of separate ferrite core elements so as to be intercepted by the plane to said test surface profile.

2. A method as claimed in claim 1, wherein the separate ferrite core elements are of elongated cylindrical form and are disposed with their longitudinal axes parallel to one another and perpendicular to the said plane.

3. A method as claimed in claim 1, wherein the ferrite core elements are of circular cross-section in the said plane and are disposed so that each element contacts its immediately adjacent element or two elements.

4. A method as claimed in any one of claims 1 to 3, wherein at least the said first coil portion includes adhesive material which is employed to adhere the first coil portion to the support member back surface and to adhere the ferrite core elements to the coil sector.

5. A method as claimed in any one of claims 1 to 3, including the step of conforming the remaining portion of the coil to the back surface constituted by the ferrite core elements to sandwich said ferrite core elements between said first portion and the remaining portion.

6. A method as claimed in any one of claims 1 to 3, including the step of encapsulating the support member, the test coil and the ferrite core elements to provide a body having a surface conforming to the said profile constituted by the support member front surface.

7. A method as claimed in any one of claims 1 to 3, including the steps of applying to the support member back surface so as to be intercepted by a plane parallel to the first-mentioned plane, and so as to conform to the profile, a first portion of a second probe electrical test coil, mounting the said plurality of separate ferrite core elements inside both of the said coils immediately adjacent to the respective first portions, and applying respective remaining portions of the last coil to said plurality of ferrite core elements to conform said respective remaining portions to the last surface.

* * * * *